United States Patent [19]

Crane

[11] Patent Number: 5,672,164
[45] Date of Patent: Sep. 30, 1997

[54] DISPOSABLE ABSORBENT ARTICLE HAVING AN EXTENDED SUBLAYER

[76] Inventor: Patrick L. Crane, 140 Aspen Lake Dr., Newnan, Ga. 32063

[21] Appl. No.: 473,962

[22] Filed: Jun. 7, 1995

[51] Int. Cl.⁶ .............. A61F 13/15; A61F 13/20
[52] U.S. Cl. ........................ 604/378; 604/385.2
[58] Field of Search ................. 604/378, 381, 604/385.1, 385.2, 386, 393, 394

[56] References Cited

U.S. PATENT DOCUMENTS

| | | |
|---|---|---|
| 3,999,547 | 12/1976 | Hernandez . |
| 4,519,798 | 5/1985 | Dinius . |
| 4,557,777 | 12/1985 | Sabee . |
| 4,704,116 | 11/1987 | Enloe . |
| 4,710,188 | 12/1987 | Runeman . |
| 4,738,675 | 4/1988 | Buckley et al. . |
| 4,778,458 | 10/1988 | Gronostajski . |
| 4,802,884 | 2/1989 | Fröidh et al. . |
| 4,808,178 | 2/1989 | Aziz et al. .............. 604/385.2 |
| 4,828,555 | 5/1989 | Hermansson . |
| 4,959,059 | 9/1990 | Eilender et al. . |
| 4,988,344 | 1/1991 | Reising et al. . |
| 5,021,051 | 6/1991 | Hiuke .............. 604/385.2 |
| 5,032,120 | 7/1991 | Freeland et al. ......... 604/385.2 |
| 5,037,409 | 8/1991 | Chen et al. . |
| 5,061,261 | 10/1991 | Suzuki et al. .......... 604/385.2 |
| 5,167,653 | 12/1992 | Igaue et al. ........... 604/385.2 |
| 5,188,626 | 2/1993 | Toyoda et al. . |
| 5,246,431 | 9/1993 | Minetola et al. ........ 604/385.1 |
| 5,246,432 | 9/1993 | Suzuki et al. .......... 604/385.1 |
| 5,263,948 | 11/1993 | Karami et al. . |
| 5,263,949 | 11/1993 | Karami et al. . |
| 5,292,316 | 3/1994 | Suzuki et al. .......... 604/385.2 |
| 5,304,161 | 4/1994 | Noel et al. . |
| 5,342,338 | 8/1994 | Roe .................. 604/358 |
| 5,342,343 | 8/1994 | Kitaoka et al. . |
| 5,352,217 | 10/1994 | Curro . |
| 5,458,591 | 10/1995 | Roessler et al. ........ 604/394 |

FOREIGN PATENT DOCUMENTS

| | | | |
|---|---|---|---|
| 6014960 | 1/1994 | Japan | 604/385.1 |
| 3012745 | 7/1993 | WIPO | 604/378 |

OTHER PUBLICATIONS

Translation of JP 406014960A Published Jan. 1994.

*Primary Examiner*—Mark O. Polutta
*Attorney, Agent, or Firm*—Baker & Botts, L.L.P.

[57] ABSTRACT

An absorbent article includes a topsheet, a backsheet and an absorbent core disposed between the topsheet and the backsheet. A sublayer is disposed between the topsheet and the absorbent core. The sublayer includes sides edges which extend past the side edges of the absorbent core and end edges which extend to the front and rear waist regions of the absorbent article. The side edges of the sublayer are secured to the backsheet in the area between the side edges of the absorbent core and the leg elastics. The attachment of the side edges of the absorbent core improves the liquid take-up by ensuring contact between the absorbent core and the sublayer even after the bond between the sublayer and the absorbent core may have failed. In addition, the attachment of the side edges to the backsheet ensures that the absorbent core maintains its shape even after it is saturated with liquid.

11 Claims, 2 Drawing Sheets

DISPOSABLE ABSORBENT ARTICLE HAVING AN EXTENDED SUBLAYER

BACKGROUND OF THE INVENTION

1. Technical Field

This invention is related to the field of disposable absorbent articles, and more particularly to disposable absorbent articles having improved liquid retention characteristics.

2. Description of the Prior Art

Prior art disposable absorbent articles are typically configured with a topsheet, a liquid impervious backsheet associated with the topsheet and an absorbent core positioned between the topsheet and backsheet. The disposable absorbent article has a front waist region, a rear waist region and a crotch region between the front and rear waist regions. A pair of leg openings are formed on either side of the disposable absorbent article in the crotch region. Leg elastics typically are positioned along the leg openings to secure the leg openings around the wearer's thighs. Permanent or releasable closure systems secure the absorbent article around the wearer's waist. Additionally, a pair of upstanding elasticized waist containment flaps are sometimes provided on opposite longitudinal sides of the bodyside surface of the topsheet.

Often, a tissue layer or sublayer is provided between the topsheet and the absorbent core. Prior art sublayers have been made from hydrophilic, non-woven material. Liquid in the topsheet is typically wicked away by the sublayer and transferred to the absorbent core.

Prior art sublayers are typically sized to have dimensions approximating the dimensions of the top of the absorbent core. The side edges of this type of sublayer do not extend beyond the side edges of the absorbent core. Instead, the sublayer is secured directly to the absorbent core, usually by an adhesive. When the absorbent core becomes saturated with liquid, the bond between the sublayer and the absorbent core is weakened, sometimes to the extent that the sublayer and the absorbent core lose contact. Such occurrences impede the transfer of liquid from the topsheet to the sublayer to the absorbent core, with the result that the wetted topsheet and sublayer sometimes remain in contact with the wearer's skin above and out of contact with the absorbent core. This phenomenon is known as "blousing." Moreover, as the absorbent core becomes more saturated with liquid, its structural integrity is degraded. Sublayers having the same profile as the top surface of the absorbent core provide little, if any, structural reinforcement to the wetted absorbent core, particularly to the side edges of the absorbent core. As the absorbent core loses its structural integrity, the liquid transfer and retention characteristics are generally diminished.

Another sublayer configuration, for instance, the sublayer configuration shown in U.S. Pat. No. 5,342,338, which is hereby incorporated by reference, includes side edges which extend past the side edges of the absorbent core. The '338 sublayer is bonded to at least 50% of the surface area of the core, whereas less than 25% of the surface area of the topsheet is joined to the sublayer between the leg cuffs. When the absorbent core in the '338 Patent becomes wetted, the bond, if any remains, between the absorbent core and the sublayer would be weakened. Thus, the sublayer in the '338 Patent may not eliminate blousing when the bond between the absorbent core and the sublayer breaks down. Consequently, the topsheet and sublayer in the '338 Patent may lose contact with the absorbent core, which in turn leads to inefficient transfer of liquid from the topsheet to the sublayer to the absorbent core. Moreover, since the '338 sublayer is designed so that less than 25% of the surface area of the topsheet is joined to the sublayer, a gap is intentionally created between the sublayer and the topsheet. This gap or space impedes the transfer of liquid from the topsheet to the absorbent core and can further result in the inefficient transfer of liquid.

These are but a few of the disadvantages of the prior art which the preferred embodiment seeks to address.

SUMMARY OF THE INVENTION

It is an object of the invention to provide a device for improving the transfer of liquid from the topsheet to the sublayer to the absorbent core.

It is a further object of the invention to provide a device for improving the structural integrity of the absorbent core after it becomes wetted.

It is a further object of the invention to provide a sublayer in an absorbent garment which quickly moves liquid from an area laterally beyond the absorbent core to an area where it can be transferred to the absorbent core.

It is still yet a further object of the invention to provide a disposable absorbent article which assures contact between the sublayer and the absorbent core even after the absorbent core becomes wetted or saturated and the bond between the absorbent core and sublayer is weakened or completely degradated.

These and other objects of the invention are achieved by a disposable absorbent article comprising a topsheet, at least a portion of which is liquid pervious, a substantially liquid impervious backsheet, and an absorbent core disposed between the topsheet and the backsheet. The absorbent article has a front waist region, a rear waist region and a crotch region positioned between the front and rear waist regions. Leg elastics are provided along the leg openings for securely holding the leg openings against the thighs of the wearer to improve containment and fit. A fastening system, either releasable or permanent, holds the absorbent article around the wearer's waist. A pair of stand-up leg gathers or waist containment flaps may be attached to or formed from the bodyside surface of the topsheet.

A substantially rectangular, non-woven, hydrophilic sublayer is positioned between the topsheet and the absorbent core. The sublayer includes first and second side edges and end edges. The end edges preferably extend to the front and rear waist regions, respectively. The side edges of the sublayer preferably terminate between the leg elastics and the side edges of the absorbent core. The side edges of the sublayer are preferably fixedly secured by, e.g. adhesive bonding, to the backsheet.

The bottom surface of the sublayer is preferably secured to the absorbent core by a plurality (e.g., three) of parallel lines of spray adhesive aligned to be parallel with the longitudinal centerline or axis of the absorbent article. The top surface of the sublayer is preferably secured to the topsheet by one or more lines of spray adhesive, preferably at least three, aligned to be parallel with the longitudinal centerline or axis of the absorbent article. Having the side edges of the sublayer extend past the side edges of the absorbent core allows for securing the sublayer to the backsheet. The strength of the bond between the sublayer and the backsheet has been found to be greater than that between the sublayer and the absorbent core, particularly after a urine insult. Moreover, it has been found that the strength of the bond between the topsheet and the sublayer is greater than the bond between the sublayer and the absorbent core. Thus, even though the sublayer may become detached from the absorbent core, the side edges of the sublayer remain bonded to the backsheet and the sublayer remains bonded to the topsheet. The continued bonding between the sublayer and the backsheet ensures that the sublayer and the topsheet do not blouse away from the absorbent core, which would otherwise impede the transfer of liquid away from the topsheet through the sublayer and ultimately into the absorbent core. Moreover, the continued bonding between the sublayer and the backsheet structurally reinforces the side edges of the absorbent core even after it becomes saturated. Thus, the structural integrity of the absorbent core is maintained, which in turn improves the liquid transfer characteristics of the absorbent core.

Moreover, since the portions of the sublayer extending outboard of the absorbent core are preferably hydrophilic, non-wovens, the sublayer wicks liquid outside the absorbent core back into the area of the absorbent core. This advantageously allows for an absorbent core having a smaller width, which in turn provides a material savings but without sacrificing the characteristics of the absorbent core.

Further objects, features and aspects of the invention will be understood from the following detailed description of the preferred embodiment with reference to the drawings.

DETAILED DESCRIPTION OF THE PREFERRED EMBODIMENT

As used herein, the term "absorbent garment" refers to garments that absorb and contain body exudates, and more specifically, refers to garments which are placed against or in proximity to the body of the wearer to absorb and contain the various exudates discharged from the body. A non-exhaustive list of examples of absorbent garments includes diapers, diaper covers, disposable diapers, trig pants, feminine hygiene products and adult incontinent briefs. The term "disposable absorbent garment" refers to absorbent garments that are intended to be discarded or partially discarded after a single use (i.e., they are not intended to be laundered or otherwise restored or reused). The term "unitary disposable absorbent garment" refers to a disposable absorbent garment that is essentially a single structure (i.e., it does not require separate manipulative parts such as a diaper cover and insert). As used herein, the term "diaper" refers to an absorbent garment generally worn by infants and incontinent persons about the lower torso.

Figure 1:
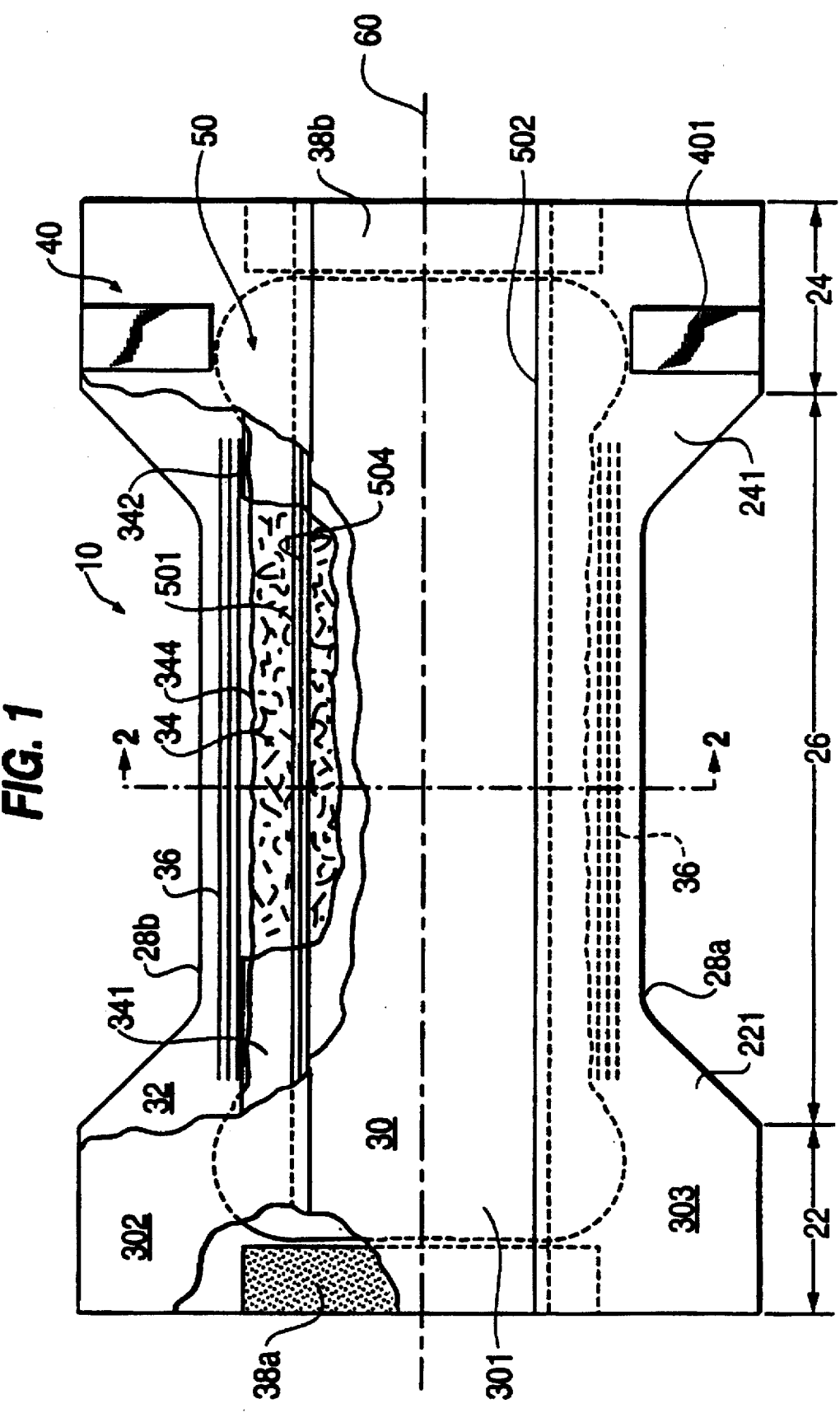
FIG. 1 is a top plan view of the absorbent garment according to the preferred embodiment with the effects of the elastics removed.

A preferred embodiment of the invention comprises a disposable absorbent garment 10, as shown in FIG. 1. It should be understood, however, that the present invention is applicable to other types of absorbent garments. For simplicity, the invention will be described in terms of a diaper. With reference to FIG. 1, the diaper 10 according to a first preferred embodiment is shown in a relaxed condition with the effects of the elastics removed for purposes of clarity in description. The diaper 10 has a generally hourglass shape and can generally be defined in terms of a front waist region 22, a back waist region 24 and a crotch region 26. Alternatively, the diaper can be configured in a generally rectangular shape. A pair of leg openings 28a, 28b extend along at least a portion of the crotch region 26. The diaper preferably comprises a topsheet 30, a backsheet 32, which may be substantially coterminous with the topsheet 30, an absorbent core 34 disposed between at least a portion of the topsheet 30 and backsheet 32, one or more pairs of leg elastics 36 (three pairs are shown in FIG. 1) extending adjacent the leg openings 28a, 28b, respectively, a front waist elastic system 38a, a back waist elastic system 38b, a fastening system 40 (e.g., tape or other suitable mechanical fastener) and a waste containment system 50 in the form of waste containment flaps 501, 502. The waste containment flaps 501, 502 preferably extend from the front waist region 22 to the back waist region 24 along opposite sides of a longitudinal centerline or axis centerline 60 of the diaper 10, or alternatively only along a portion thereof. The front waist region 22 and rear waist region 24 include ear portions 221, 241 extending outwardly from the leg openings 28a, 28b.

Figure 2:
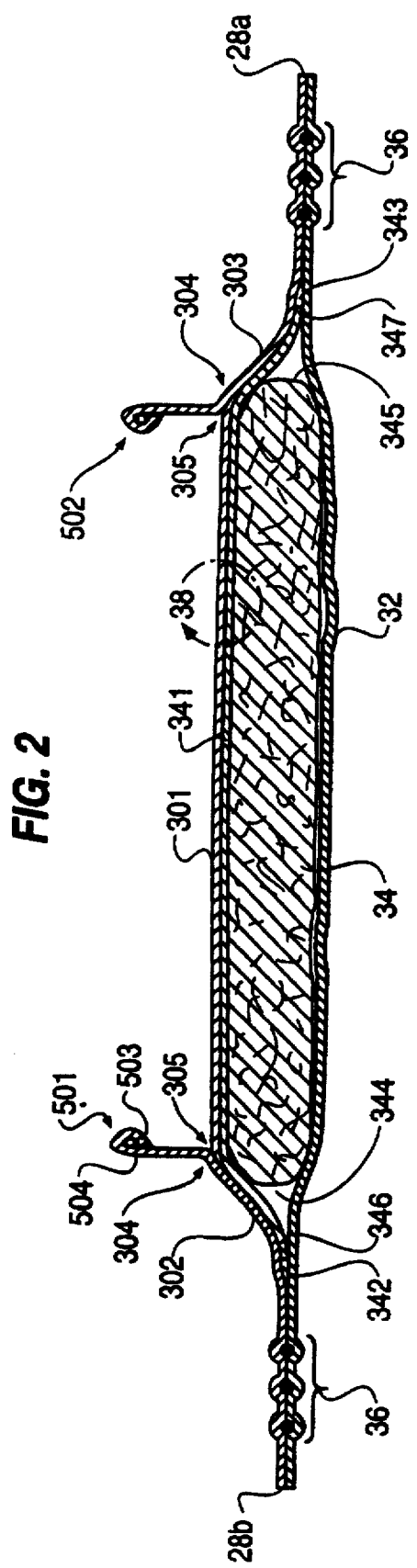
FIG. 2 is a cross section taken along line 2—2 in FIG. 1.

With reference to FIG. 2 in conjunction with FIG. 1, the topsheet 30 is preferably formed of three separate portions or panels. The first panel comprises a central topsheet panel 301. The central topsheet panel 301 is preferably a liquid pervious material that is either hydrophobic or hydrophilic. The central topsheet panel may be made from any number of materials, including synthetic fibers (e.g., polyester or polypropylene fibers), natural fibers (e.g., wood or cellulose), apertured plastic films, reticulated foams and porous foams to name a few. One preferred material for the central topsheet panel 301 is a coverstock of single ply nonwoven material which may be made of carded fibers, either adhesively or thermally bonded, perforated plastic film, spun bonded fibers, or water entangled fibers, which generally weigh from 0.3–0.7 oz./sq. yd. and have appropriate and effective machine-direction and cross-machine direction strength suitable for use as a baby diaper coverstock material. The central topsheet panel 301 preferably extends from substantially the front waist region 22 to the back waist region 24 or a portion thereof.

The second and third topsheet panels 302, 303 are positioned laterally outside the central topsheet panel 301. The outer topsheet panels 302, 303 are preferably substantially liquid impervious and hydrophobic, preferably at least in the crotch area. The outer edges of panels 302, 303 may substantially follow the corresponding outer perimeter of the backsheet 32. The material for the outer topsheet portions or panels 302, 303 is preferably polypropylene and can be woven, nonwoven, spunbonded, carded, or the like, depending on the application.

The inner edges 304 of the outer topsheet portions or panels 302, 303 preferably are attached by, e.g., an adhesive, to the outer edges 305 of the inner topsheet portion or panel 301. At the point of connection with the outer edges 305 of the inner topsheet portion or panel 301, the inner edges 304 of the outer topsheet portions or panels 302, 303 extend upwardly to form waist containment flaps 501,502. The waste containment flaps 501,502 are preferably formed of the same material as the outer topsheet portions or panels 302, 303, as in the embodiment shown they are simply an extension of the outer topsheet portions or panels 302, 303. The waste containment flaps 501,502 may be treated with a suitable surfactant to modify their hydrophobicity/hydrophilicity as desired. Alternatively, the waste containment flaps 501,502 may be formed as separate elements and then attached to the bodyside liner. In this alternative embodiment, the central topsheet portion or panel 301 may extend past the connection point with the waste containment flaps, and even extend to the periphery of the backsheet. Still further, the central topsheet portion or panel 301 could extend fully between the outer topsheet portions or panels 302, 303 and the sublayer 341 and even beyond so that the outer edges 305 of the central topsheet portion or panel 301 are coextensive with and sandwiched between the outer topsheet portions or panels 302, 303 and the backsheet 32.

The waste containment flaps 501,502 preferably include a portion 503 which folds over onto itself to form a small enclosure. At least one, and depending on the size of the enclosure sometimes more than one, elastic member 504 is secured in the enclosure in a stretched condition. As has been known at least as long as the disclosure of Tetsujiro, Japanese Patent Document 40-11543, when the flap elastic 504 attempts to assume the relaxed, unstretched condition, the waste containment flaps 501,502 rise above the surface of the central topsheet portion or panel 301.

Absorbent core 34 is preferably positioned beneath at least the central topsheet portion or panel 301 (or a portion thereof), and more preferably is also positioned beneath a portion of the outer topsheet portions or panels 302, 303. A substantially rectangular, preferably non-woven, sublayer 341 having a basis weight of about 0.1-2 oz., preferably about 0.4-0.6 oz., overlays absorbent core 34. While the absorbent core 34 is shown as having a somewhat hourglass shape, other shapes are within the scope of the preferred embodiment. For example, the absorbent core 34 may have a rectangular shape of substantially the same size as the central topsheet portion or panel 301 or an asymmetric shape.

Examples of suitable materials for the absorbent core 34 include creped cellulose wadding, absorbent foams, absorbent sponges, super absorbent polymers, absorbent gelling materials, fiberized cellulose, fluff pulp having tissue or synthetic materials between the absorbent core 34 and the hydrophilic topsheet 301 or any equivalent material or combination of materials. The size and capacity of the absorbent material should correspond to the application, i.e., an incontinent brief for an adult requires a larger absorbent core than a diaper for a child. Zoned absorbency may also be used if desired. For example, more absorbency may be used in particular regions depending on the gender of the intended wearer.

A backsheet 32 is associated with the topsheet 30. As used herein, the term "associated" encompasses configurations whereby the topsheet 30 is directly joined to the backsheet 32 by affixing the topsheet 30 directly to the backsheet 32, and configurations whereby the topsheet 30 is indirectly joined to the backsheet 32 by affixing the topsheet 30 through intermediate members which in turn are affixed to the backsheet 32. The backsheet 32 may be made from a low density polyethylene about 0.01 min. to about 0.3 min. thick, preferably with a thickness of about 0.03 mm. Other backsheet materials will be readily apparent to those skilled in the art. A backsheet having a longitudinal dimension of about 45 cm., a transverse dimension at the front and back waist regions 22, 24 of about 32 cm. and a transverse dimension through the central crotch region 26 of about 20 cm. is suitable for one application. While the backsheet 32 and topsheet 30 in the preferred embodiment have substantially the same dimensions, they may also have different dimensions.

In addition, the backsheet 32 may be covered with a fibrous nonwoven fabric such as is disclosed in U.S. Pat. No. 4,646,362 to Heran, which is hereby incorporated by reference. Materials for such a fibrous outer liner include a spun-bonded nonwoven web of synthetic fibers such as polypropylene, polyethylene or polyester fibers; a nonwoven web of cellulosic fibers, textile fibers such as rayon fibers, cotton and the like, or a blend of cellulosic and textile fibers; a spun-bonded nonwoven web of synthetic fibers such as polypropylene, polyethylene or polyester fibers mixed with cellulosic, pulp fibers, or textile fibers; or melt blown thermoplastic fibers, such as macrofibers or microfibers, of polypropylene, polyethylene, polyester or other thermoplastic materials or mixtures of such thermoplastic macrofibers or microfibers with cellulosic, pulp or textile fibers. The fibrous backing sheet is particularly suitable in trig pants applications since, while the child is still protected against accidents, the training pants have the look and feel of cloth.

The underlying structure beneath the topsheet 30 can include, depending on the diaper construction, various combinations of elements, but in each an extended sublayer 341 is contemplated. For example, the underlying structure beneath the topsheet 30 might include the following combinations of elements: a backsheet and an extended sublayer; a backsheet, an absorbent core and an extended sublayer; a backsheet, a fibrous non-woven layer, an absorbent core and an extended sublayer; to name a few. Moreover, depending on the particular location on the topsheet, the underlying structure might differ even in the same diaper. This is apparent, for example, in FIG. 2 wherein the underlying structure beneath the central topsheet portion or panel 301 proximate to the longitudinal centerline 60 includes backsheet 32, absorbent core 34 and extended sublayer 341, whereas proximate to the leg openings 28a, 28b, the underlying structure includes backsheet 32 and leg elastics 36. As used herein, the term "underlying structure" refers generally to the foregoing elements alone or in combination, unless otherwise specified.

Each leg opening 28a, 28b is provided with a leg elastic containment system 36. In the preferred embodiment, three strands of elastic threads are positioned to extend adjacent the leg openings 28a, 28b between the outer topsheet portions or panels 302, 303 and the backsheet 32. Any suitable elastomeric material exhibiting at least an elongation (defined herein as Ls-Lr/Lr where Ls is the stretched length of an elastic element and Lr is retracted length, multiplied by 100 to obtain percent elongation) in the range of 5% to 350%, preferably in the range of 200% to 300%, can be employed for the leg elastics 36. The leg elastics 36 may be attached to the diaper 10 in any of several ways which are known in the art. For example, the leg elastics 36 may be ultrasonically bonded, heat/pressure sealed using a variety of bonding patterns, or glued to the diaper 10.

Various commercially available materials can be used for the leg elastics 36, such as natural rubber, butyl rubber or other synthetic rubber, urethane elastomeric material such as that available from B. F. Goodrich Co. under the trademark TUFTANE, and elastomeric material available from H. B. Fuller Co. under the tradename FULLASTIC. The latter material (see e.g., U.S. Pat. No. 4,418,123) is based upon thermoplastic elastomeric copolymers of the A-B-A type such as those available from Shell Chemical Co. under the trademark KRATON which have a rubbery midblock such as butadiene or isoprene and polystyrene end blocks, and is especially useful because it is a self-adhesive material and can be applied to the portions or panels of the garment without additional adhesive between the elastic means and the portions or panels.

The fastening system 40 of the preferred embodiment is attached to the back waist region 24, and preferably comprises tape tab or mechanical fasteners 401. However, any fastening system known in the art will be acceptable. Moreover, the fastening system 40 may include a reinforcement patch below the front waist portion so that the diaper may be checked for soiling without compromising the ability to reuse the fastener. Alternatively, other diaper fastening systems are also possible, including safety pins, buttons, and snaps.

Waist elastics 38a, 38b may be similar structures or different to impart similar or different elastic characteristics to the front and back waist portions of the diaper. In general, the waist elastics may comprise foam strips 38 positioned at the front and back waist sections 22, 24. The foam strips 38 are preferably about ½ to 1½ inches wide and about three to six inches long. The foam strips 38 are preferably positioned between the topsheet portions or panels 301, 302, 303 and the backsheet 32. The foam strips 38 are preferably polyurethane, but could be any other suitable material which decreases waistband roll over, reduces leakage over the waist ends of the absorbent garment, and generally improves comfort and fit. The front and back waist foam strips 38a, 38b are stretched 50–150%, preferably 100%, before being adhesively secured between the backsheet 32 and the topsheet 30.

The central topsheet panel 301 is preferably bonded to the sublayer 341 in three distinct bond areas spaced about ½ inch apart, each of which comprises approximately one inch wide lines of adhesive applied by circular spray application or some other adhesive application known in the art. The type of adhesive used for the topsheet/sublayer bond is preferably any suitable hydrophilic adhesive, for instance Cycloflex as sold by National Starch. The three topsheet/sublayer lines of adhesive preferably extend substantially parallel to the longitudinal centerline 60 of the absorbent garment. Additionally, the topsheet/sublayer lines of adhesive are preferably equi-distant from one another so that the central line 60 of adhesive substantially follows the longitudinal center line 60 of the absorbent garment.

The sublayer 341 and the absorbent core 34 immediately therebelow are also preferably adhesively bonded, again with any suitable hydrophilic adhesive in three distinct bond areas, each of which comprises approximately one inch wide lines of adhesive applied by circular spray application or some other adhesive application known in the art. The three sublayer/absorbent core lines of adhesive are preferably about ½ inch apart from one another and preferably extend substantially parallel to the longitudinal centerline 60 of the absorbent garment.

In one alternative configuration, the bond area co/meeting the central topsheet panel 301 to the sublayer 341 is limited to the central-most portion of the sublayer 341. For instance, in the case where a four inch wide absorbent core is employed, the lines of adhesive between the central topsheet panel 301 and the sublayer 341 may comprise a 2 or 2½ inch wide adhesive area extending along the longitudinal centerline of the absorbent garment, i.e., no adhesive subjacent the waist containment flaps 501,502. Similarly, the outer topsheet panels 302, 303 are likewise not bonded to the sublayer 341 subjacent the waist containment flaps 501, 502. At its side edges 342, 343, the sublayer 341 is then attached to the backsheet between the side edges 344, 345 of the absorbent core 34 and the leg elastics 36. By eliminating the topsheet/sublayer core bond area subjacent the waist containment flaps, the waist containment flaps 501,502 rise above the plane surface of the absorbent core 34 under the influence of the elastics 504 positioned within enclosure 503. That the waist containment flaps 501, 502 rise above the surface of the absorbent core permits a smaller flap to be used without compromising the containment characteristics of a larger flap. In other words, as the flaps rise above the surface of the absorbent core, they take on the characteristics of a larger, i.e., taller, flap when preventing the lateral flow of body exudates. Accordingly, where a shorter flap without subjacent adhesive between the sublayer and the absorbent core is employed, a material savings is realized over the configuration where a taller flap having subjacent adhesive prevents the same from rising above the surface of the absorbent core.

The sublayer 341 is preferably treated with any suitable surfactant known in the art so that it is or becomes hydrophilic and liquid pervious. The side edges 342, 343 of the sublayer 341 preferably extend past the side edges 344, 345 of the absorbent core 34, at least in the crotch area 26, but preferably substantially along the entire length of the absorbent core 34. The side edges 342, 343 of the sublayer 341 are preferably located between the side edges 344, 345 of the absorbent core 34 and the leg elastics 36. In this area, the side edges 342, 343 of the sublayer 341 are bonded, either adhesively, ultrasonically or by any other known method of bonding, directly to the backsheet 32 at 346, 347. The extended portion of the sublayer 341, which is also preferably made of a hydrophilic, spun-bonded, non-woven advantageously wicks liquid back to the absorbent core where it can be more efficiently absorbed. Thus, the provision of extending the sublayer 341 allows for a material savings in the absorbent core, but without sacrificing the liquid take-up capacity of the absorbent garment as a whole.

In addition to improving liquid take-up characteristics while providing a material savings to the absorbent core, the extended sublayer of the preferred embodiment advantageously maintains the structural integrity of the absorbent core after it becomes saturated, particularly in the side edges 344, 345 of the absorbent core 34. Moreover, since the sublayer/backsheet bond and sublayer/topsheet bond are both stronger than the sublayer/absorbent core bond, even if the sublayer/absorbent core bond breaks down, the other bonds are sufficient to keep the sublayer in contact with the absorbent core. Consequently, blousing is eliminated, and an efficient transfer of liquid from the topsheet to the sublayer to the absorbent core is maintained in the event of multiple urine insults.

In each of the preferred embodiments, the central topsheet portion or panel 301, outer topsheet portions or panels 302, 303 and the sublayer 341 are preferably bonded to the elements therebelow with adhesive glue applied by spraying. Alternatively, any of these elements could be spot glued, ultrasonically bonded, or secured in any other manner known in the art.

In any or all of the foregoing embodiments, the topsheet may comprise a single sheet of material having different characteristics (e.g. liquid imperviousness/perviousness and or hydrophobicity/hydrophilicity) and have regions of transition or demarcation therebetween.

The invention has been described in connection with the preferred embodiment. This embodiment, however, is merely for example only and the invention is not restricted thereto. It will be understood by those skilled in the art that other variations and modifications can easily be made within the scope of the invention as defined by the appended claims.

I claim:

1. A disposable absorbent article having a front waist region, a rear waist region and a crotch region, said absorbent article comprising:
   a backsheet;
   a topsheet associated with said backsheet;
   an absorbent core disposed between said backsheet and said topsheet, said absorbent core having spaced side edges and end edges;

a front waist region;

a rear waist region;

a crotch region between said front and rear waist regions;

a pair of leg openings intermediate the front and rear waist regions;

leg elastics positioned adjacent said leg openings;

said topsheet further comprising a central panel and a pair of outboard panels, each of said outboard topsheet panels having a first portion and a second portion integrally formed with and extending from said first portion, said second portion comprising an upstanding waste containment flap attached to said central topsheet panel above said absorbent core; and a sublayer positioned between said topsheet and said absorbent core, said sublayer having side edges extending beyond said side edges of said absorbent core, said side edges of said sublayer bonded to said backsheet between said side edges of said absorbent core and said leg elastics.

2. The disposable absorbent article according to claim 1, said sublayer comprising a hydrophilic, spun-bonded, non-woven liquid pervious material.

3. The disposable absorbent article according to claim 1, said sublayer extending from said front waist region to said rear waist region.

4. The disposable absorbent article according to claim 1, wherein said waste containment flaps are elasticized and positioned on opposite sides of a longitudinal centerline of the absorbent article.

5. The disposable absorbent article according to claim 4, said waste containment means positioned above said absorbent core in at least the crotch region.

6. The disposable absorbent article according to claim 1, said central topsheet panel having a width dimension equal to or smaller than a width dimension of said absorbent core.

7. The disposable absorbent article according to claim 1, said outer topsheet panels comprising hydrophobic substantially liquid impervious non-woven material.

8. The disposable absorbent article according to claim 1, further comprising bond means for bonding said sublayer to said absorbent core.

9. The disposable absorbent article according to claim 2, said absorbent article having a longitudinal centerline, said bond means for bonding said sublayer to said absorbent core comprising three substantially equally spaced lines of adhesive extending parallel to the longitudinal centerline of the absorbent article.

10. The disposable absorbent article according to claim 1, further comprising bond means for bonding said topsheet to said sublayer.

11. The disposable absorbent article according to claim 10, said absorbent article having a longitudinal centerline, said bond means for bonding said topsheet to said sublayer comprising two lines of adhesive extending parallel along opposite sides of the longitudinal centerline of the absorbent article.

* * * * *